US010485979B2

(12) United States Patent
Guyon et al.

(10) Patent No.: US 10,485,979 B2
(45) Date of Patent: Nov. 26, 2019

(54) INTEGRATED POWER DELIVERY, COMMUNICATION, AND HEALTH MONITORING SYSTEM FOR IMPLANTABLE ELECTRODE

(71) Applicant: The Charles Stark Draper Laboratory, Inc., Cambridge, MA (US)

(72) Inventors: Daniel Guyon, Arlington, MA (US); Brent Hollosi, Medford, MA (US); John R. Lachapelle, Princeton, MA (US); Brian Nugent, Acton, MA (US); Matthew Muresan, Somerville, MA (US); Jesse J. Wheeler, East Boston, MA (US); Andrew Czarnecki, Cambridge, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 97 days.

(21) Appl. No.: 15/439,439

(22) Filed: Feb. 22, 2017

(65) Prior Publication Data
US 2017/0239485 A1 Aug. 24, 2017

Related U.S. Application Data
(60) Provisional application No. 62/298,190, filed on Feb. 22, 2016.

(51) Int. Cl.
*A61N 1/36* (2006.01)
*A61N 1/372* (2006.01)
(Continued)

(52) U.S. Cl.
CPC ....... *A61N 1/37217* (2013.01); *A61N 1/0551* (2013.01); *A61N 1/08* (2013.01); *A61N 1/3605* (2013.01); *A61N 1/3787* (2013.01)

(58) Field of Classification Search
CPC .. A61N 1/08; A61N 1/37127; A61N 1/36125; A61N 1/36128
See application file for complete search history.

(56) References Cited

U.S. PATENT DOCUMENTS

| 2006/0083257 A1* | 4/2006 | Price | H04L 1/16 370/444 |
|---|---|---|---|
| 2007/0255319 A1 | 11/2007 | Greenberg et al. | |

(Continued)

OTHER PUBLICATIONS

International Search Report and Written Opinion dated May 4, 2017 in PCT Application No. PCT/US2017/018878.
(Continued)

*Primary Examiner* — George R Evanisko
(74) *Attorney, Agent, or Firm* — McDermott Will & Emery LLP

(57) ABSTRACT

The present disclosure describes systems and methods for improving the safety of bio-implantable electronics systems used for recording and electrical stimulation applications. The present disclosure discusses a communication protocol that provides DC balanced, bi-directional communication between a controller hub and satellite electrical stimulation and recording devices distributed throughout the patient's body. The present disclosure also describes a system for detecting and preventing current leaks along electrical pathways that may pass into a patient.

15 Claims, 5 Drawing Sheets

(51) Int. Cl.
*A61N 1/08* (2006.01)
*A61N 1/378* (2006.01)
*A61N 1/05* (2006.01)

(56) References Cited

U.S. PATENT DOCUMENTS

| | | | | |
|---|---|---|---|---|
| 2010/0204766 | A1* | 8/2010 | Zdeblick | A61B 5/0422 |
| | | | | 607/119 |
| 2011/0022113 | A1 | 1/2011 | Zdeblick et al. | |
| 2011/0069965 | A1* | 3/2011 | Kim | H04B 10/1149 |
| | | | | 398/130 |
| 2013/0073002 | A1* | 3/2013 | Nygard | A61N 1/378 |
| | | | | 607/57 |
| 2015/0360028 | A1* | 12/2015 | Tsampazis | A61N 1/36032 |
| | | | | 607/57 |
| 2016/0038739 | A1* | 2/2016 | Liu | A61N 1/3787 |
| | | | | 607/45 |

OTHER PUBLICATIONS

Wheeler, Jesse J. et al., An implantable 64-channel neural interface with reconfigurable recording and stimulation, In Engineering in Medicine and Biology Society (EMBC), 37th Annual International Conference of the IEEE pp. 7837-7840, Aug. 25, 2015.

\* cited by examiner

INTEGRATED POWER DELIVERY, COMMUNICATION, AND HEALTH MONITORING SYSTEM FOR IMPLANTABLE ELECTRODE

CROSS-REFERENCE TO RELATED APPLICATIONS

This application claims priority to Provisional U.S. Patent Application No. 62/298,190, entitled "Integrated Power Delivery, Communication, and Health Monitoring System for Implantable Electrode," filed Feb. 22, 2016, the entirety of which is incorporated herein by reference.

GOVERNMENT LICENSE RIGHTS

This invention was made with government support under N66001-15-C-4019 awarded by the Defense Advanced Research Project Agency (DARPA). The government has certain rights in the invention.

BACKGROUND

Peripheral and cortical neural stimulation are increasingly popular disease treatments. Peripheral and cortical neural stimulation devices function by delivering electrical stimulation to target tissue, which elicits a physiological response. Electrical stimulation has been used to treat chronic pain, migraines, Parkinson's disease, and depression.

Implantable electrical systems, such as peripheral and cortical neural stimulation devices, can develop electrical faults that cause leakage current to drain into the patient. The leakage current can cause injury or death to the patient. To prevent leakage current medical devices typically do not include a single point of failure and often include capacitors at each of the device's output pins. The requirement to include capacitors at each output pin can prevent the miniaturization of the implantable electronic device.

SUMMARY OF THE DISCLOSURE

The present disclosure describes systems and methods for improving the safety of implantable electronics systems used for recording and electrical stimulation applications. According to one aspect of the disclosure, an implantable neural interface system includes a controller hub and a plurality of satellite devices. The controller hub includes a first communication chip. Each of the plurality of satellite devices are coupled to the controller hub. The satellite devices include an output pathway to an electrode. The satellite devices also include a leakage current monitor that is coupled to the output pathway and is configured to detect a leakage current along the output pathway. The satellite devices also include a second communication chip that is configured to send and receive communication signals from the first communication chip.

In some implementations, each of the plurality of satellite devices are coupled to the controller hub along a single cable. In some implementations, the first and second communication chips are configured to communicate using a 3-wire protocol.

In some implementations, the communication signals are encoded and decoded using a DC-balanced encoding scheme. The DC-balanced encoding scheme can be a 4b6b encoding scheme.

In some implementations, the leakage current monitor is configured to divert power away from a corresponding electrode responsive to detecting leakage current above a threshold along the output pathway. In some implementations, the leakage current monitor is configured to cause a message to be transmitted to the controller hub indicating a detected current leakage responsive to detecting leakage current above a threshold along the output pathway. In some implementations, the controller hub is configured to, responsive to receiving a message indicating the detected leakage current, transmit a warning message to a receiver located external to the subject. The leakage current monitor can include two electrostatic discharge (ESD) diodes coupled to the output pathway. The leakage current monitor can also include an analog-to-digital converter coupled across a resistor coupled to one of the ESD diodes.

According to another aspect, the invention relates to a method of interfacing with a nerve of a subject. The method includes implanting a controller hub in a first location within the subject. The controller hub includes a first communication chip. The method further includes implanting a satellite device in a second location in the subject. The satellite device includes a second communication chip and is implanted such that the satellite device is in communication with the controller hub via the first communication chip and the second communication chip. At least one electrode coupled to the satellite via a satellite output pathway is coupled to the nerve of the subject. The satellite output pathway is monitored for a leakage current.

In some implementations, the method further includes, in response to detecting a leakage current over a threshold, diverting power away from the satellite output pathway. In some implementations, the method further includes, in response to detecting a leakage current over a threshold, causing the satellite to transmit a message to the controller hub indicating a detected current leakage. In some such implementations, responsive to the controller hub receiving a message indicating the detected leakage current, the method includes transmitting by the controller hub, a warning message to a receiver located external to the subject. In some implementations, monitoring the output pathway for a leakage current comprises measuring an analog voltage across a resistor coupled to an electrostatic discharge (ESD) diode.

In some implementations, the method further includes implanting a second satellite device coupled to the controller hub in a third location within the subject, and the satellite device and the second satellite device couple to the controller hub along a single cable. In some implementations, the satellite and the controller hub communicate using a 3-wire protocol. In some implementations, the first and second communication chips are configured to encode and decode the communication signals using a DC-balanced encoding scheme. In some such implementations, the DC-balanced encoding scheme is a 4b6b encoding scheme.

The foregoing general description and following description of the drawings and detailed description are exemplary and explanatory and are intended to provide further explanation of the invention as claimed. Other objects, advantages, and novel features will be readily apparent to those skilled in the art from the following brief description of the drawings and detailed description of the invention.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale; emphasis instead being placed upon illustrating the principles of the teachings. The drawings are not intended to limit the scope of the present teachings in any way. The system and method may be better understood from the following illustrative description with reference to the following drawings in which.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

The present disclosure describes systems and methods for improving the safety of implantable electronics systems used for recording and electrical stimulation applications. The present disclosure discusses a communication protocol that provides DC balanced, bi-directional communication between a controller hub and satellite devices distributed in different regions within a patient's body. The present disclosure also describes a system for detecting and preventing current leaks along electrical pathways that may pass into a patient.

Figure 1:
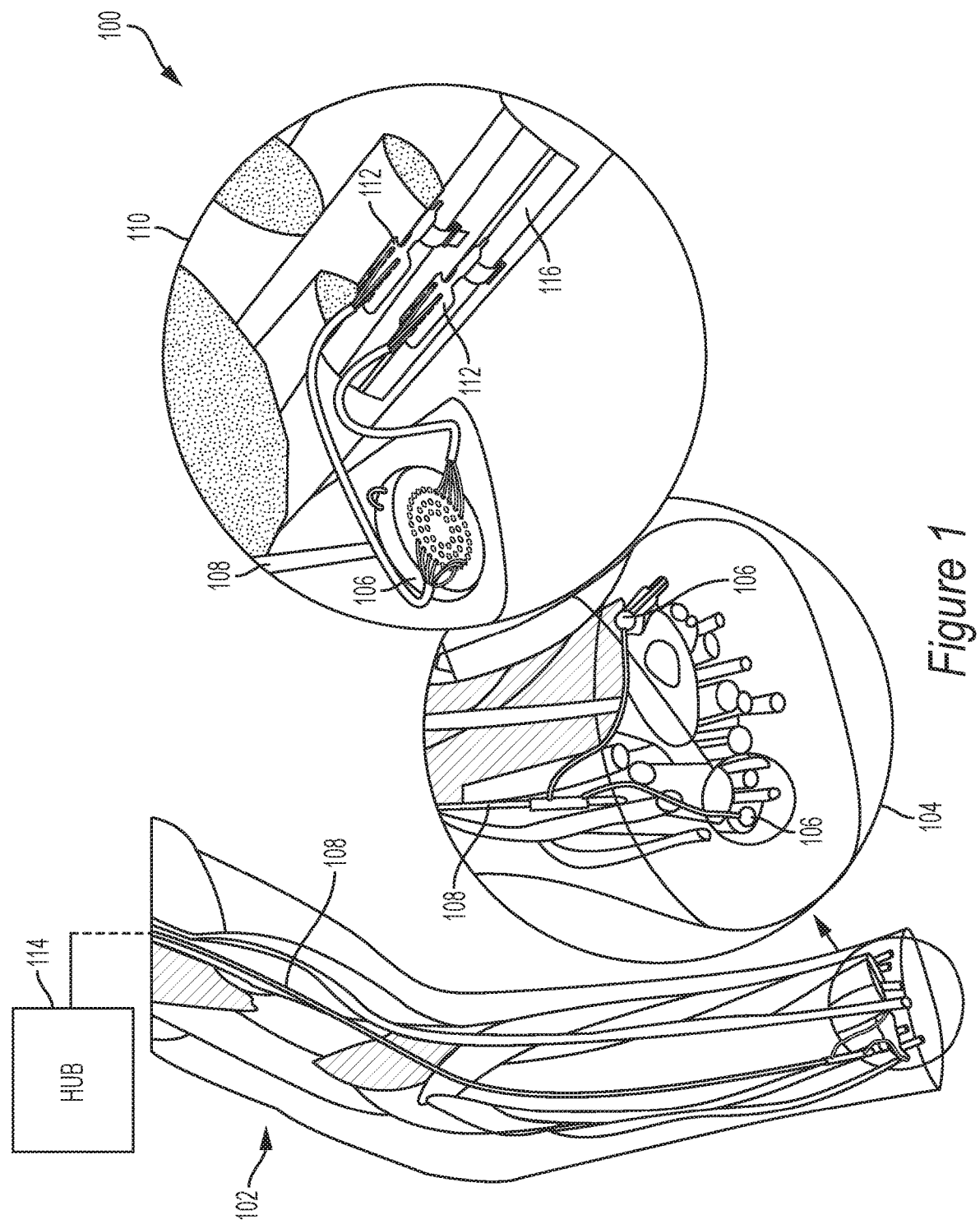
FIG. 1 illustrates an example system for peripheral nerve stimulation and recording.

FIG. 1 illustrates an example system 100 for peripheral nerve stimulation and recording. While the system 100 can be implanted anywhere in the body, FIG. 1 illustrates a portion of the system 100 implanted in the right arm 102 of a patient. The enlarged portion 104 illustrates that two satellites 106 are coupled to a controller hub 114 via a connector 108. The second enlarged portion 110 illustrates that two electrodes 112 are coupled to one of the satellites 106. Each of the electrodes 112 is coupled to a peripheral nerve fascicle 116 in the wrist of the arm 102.

As an overview of the system architecture, The system 100 includes a central controller hub 114 that is implanted into a central location, such as in a surgically created sub-dermal pocket in the upper arm or chest. The satellites 106 are implanted near target tissue, such as the nerve fascicle 116. The satellites 106 are coupled to the controller hub 114 by a single connector 108. The coupling of the hub 114 to multiple satellites 106 is described further in relation to FIG. 3. The satellites 106 interface with the never fascicle's 116 nerve fibers via the electrodes 112. Power is provided to the satellites 106 and electrodes 112 by the controller hub 114 via an alternating current (AC) signal over the connector 108. The satellites 106 enable the electrodes 112 to be configured in real-time for recording or stimulation. The satellites 106 also include a neural amplifier with an embedded analog to digital converter that enables recording and digital transmission of neural signals captured by the electrodes 112. The hub 114 or satellite 106 includes stimulation channels for stimulating target tissue via the electrodes 112, one or more processors for adaptive closed-loop control, bidirectional wireless data telemetry for communication with an external base station, and a wirelessly rechargeable lithium battery for power.

The system 100 includes one or more electrodes 112 coupled to each of the satellites 106. The electrodes 112 provide the interface between the system 100 and the patient. The electrodes 112 are configured to be secured directly to a patient's nerve fascicle or other neural tissue. The electrode 112 includes a plurality of electrode sites distributed along an elongated projection that extends from the body of the electrode. In some implementations, the elongated projection is configured for implantation through a peripheral nerve fascicle to record (and stimulate) from different nerve fibers within the central portion of the nerve fascicle.

Figure 2:
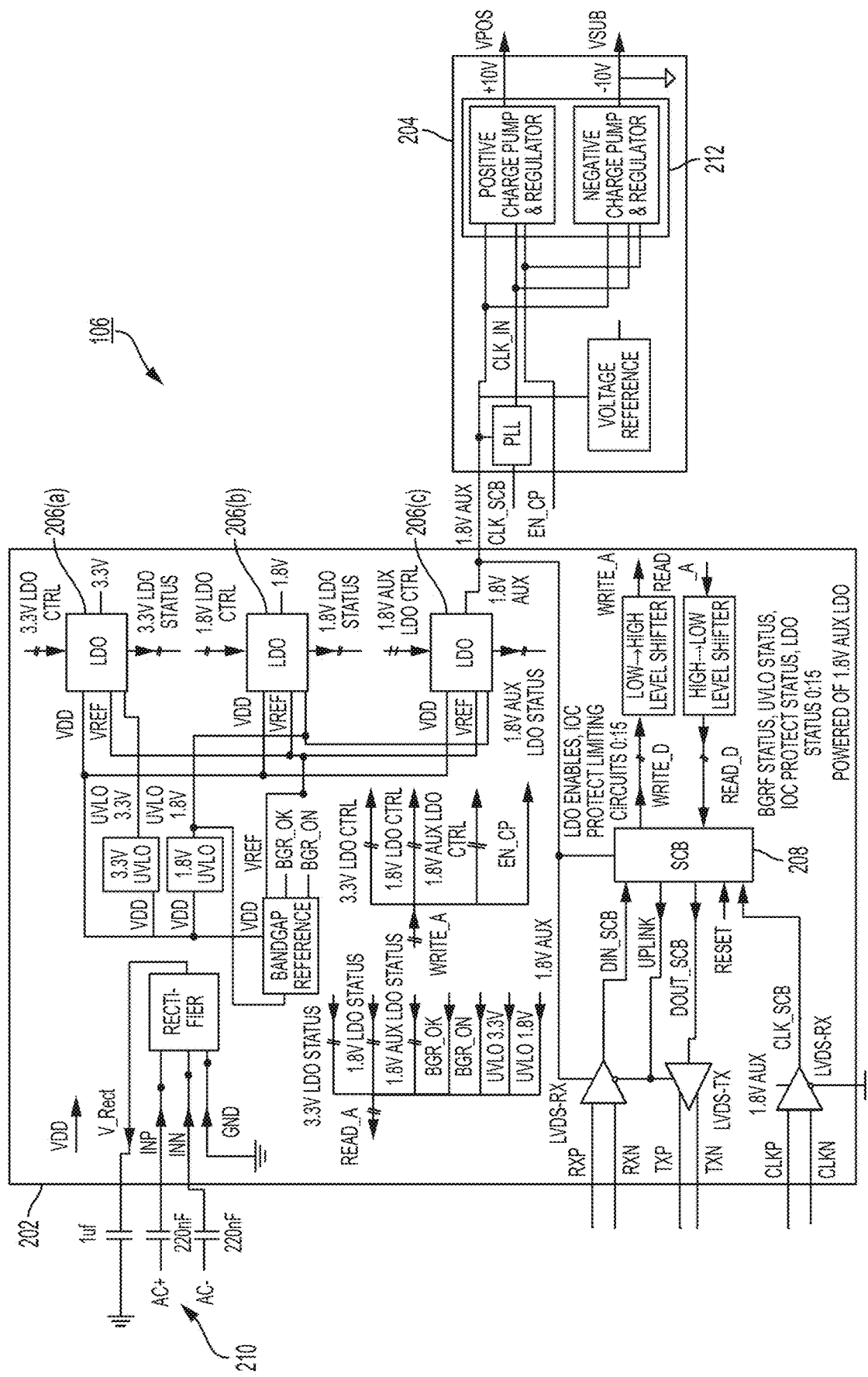
FIG. 2 illustrates a schematic of an example satellite for use with the system illustrated in FIG. 1.

FIG. 2 illustrates a schematic of the satellite 106. The satellite 106 includes a first integrated circuit (IC) 202 and a second IC 204. The IC 202 is responsible for AC-DC conversion, bi-directional communication, health monitoring (e.g., the detection of leakage current) of satellite 106, and the creation of three low voltage outputs. The IC 204 generates two bipolar high voltage outputs. To provide a DC-balanced system, the satellite 106 includes pairs of power, communication, and clock lines. In some implementations, the satellite 106 includes seven inputs—two AC power lines, two bi-directional communication lines, two complimentary clock lines, and a ground reference. In some implementations, reducing the wire count in an implantable system is beneficial because it reduces the failure points of the system.

The IC 202 includes three low-dropout (LDO) regulators 206(a)-206(c) (collectively referred to as the LDOs 206). The IC 202 also includes a serial communication bus (SCB) 208. Each of the LDOs 206 is configured to generate a different DC power level from the AC waveforms received from the AC input lines 210. The generated DC power is supplied to the different components of the IC 202 and the satellite 106. The LDO 206(a) is configured to generate a 3.3 V DC voltage, the LDO 206(b) is configured to generate a 1.8 V DC voltage, and the LDO 206(c) is configured to generate a 1.8 V auxiliary DC voltage. In other implementations, the LDOs 206 can generate other voltages without departing from the scope of the disclosures.

The IC 202 also includes a SCB 208. The SCB 208 is a DC-balanced, bi-directional communication chip. As used herein, the term chip refers to an integrated circuit device, such as an application specific integrated circuit (ASIC), field programmable gate array (FPGA), microprocessor, or other general or special purpose processing device. The SCB 208 is used as a two-way communication link between the satellite 106 and the hub 114. For example, the hub 114 can send program settings to the satellite 106 via the SCB 208 and the satellites 106 can transmit data recorded with an electrode 112 coupled to the satellite 106 back to the hub 114. Health and status information about the satellite 106 can also be transmitted back to the hub 114 via the SCB 208. The communication protocol used by the SCB 208 is described further in relation to FIG. 3.

The IC 204 includes a charge pump 212. The charge pump 212 is configured to generate a ±10 V DC voltage. In some implementations, the ±10 V waveform is used for electrically stimulating a target tissue through an electrode 112 coupled to the satellite 106. In some implementations, the substrate bias of the IC 202 and IC 204 can be controlled during the assembly process to control the system's ground reference. For example, the system's ground can be −10 V or one of the IC 202 and 204 ground reference. In some implementations, the charge pump 212 can be configured to output voltages of other magnitudes, e.g., ±5 V, ±15 V, ±20V, or ±25V.

Figure 3:
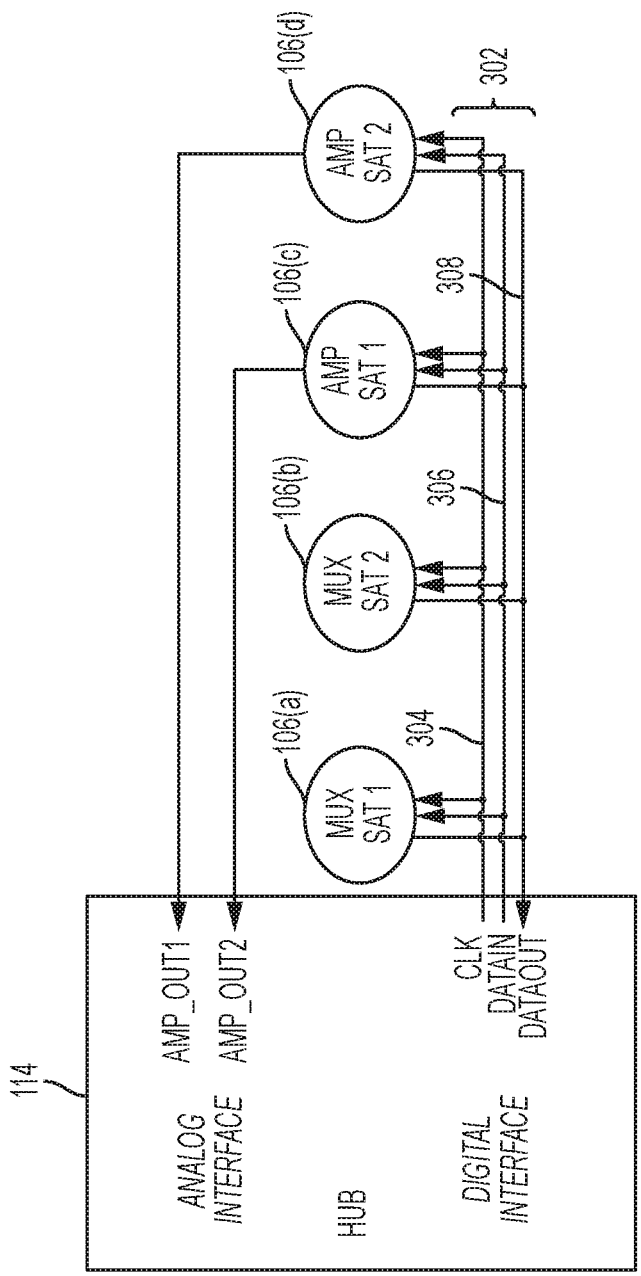
FIG. 3 illustrates a schematic of an example communication topology between a hub and a plurality of satellites.

FIG. 3 illustrates a schematic of an example communication topology between a hub 114 and a plurality of satellites 106. As illustrated, the hub 114 is coupled to four satellites 106 (e.g., satellites 106(a)-106(d)). The satellites 106 communicate with the hub 114 through a single cable 302 that includes three channels—a clock line 304, a data in line 306, and a data out line 308. In some implementations, each of the hub 114 and the satellites 106 includes one of the above-described SCBs 208. In some implementations, the cable 302 can include fewer than three channels, and in other implementations, the cable 302 can include more than three channels. For illustrative purposes, FIG. 3 illustrates four satellites 106 coupled to the hub 114. In other implementations, hundreds of satellites 106 can be coupled to the hub 114 by the single cable 302. For example, the system can include between about 1 and about 250, between about 1 and about 200, between about 1 and about 150, or between about 1 and about 100 satellites 106.

In some implementations, the SCB 208 uses a 3-wire protocol to enable DC-free communication between the hub 114 and satellites 106. The SCB 208 implements a bit protocol over the data lines 306 and 308 that employs a 4b6b encoding scheme. The 4b6b encoding scheme is DC-balanced. In a 4b6b encoding scheme, the transmitting SCB 208 maps 4-bit symbols to 6-bit symbols, and the receiving SCB 208 maps the 6-bit symbols back to 4-bit symbols. The 4b6b encoding scheme is DC-balanced because, in a sufficiently long string, the number of 0's and 1's in the string are equal. In some implementations, the SCB 208 employs an 8b10b scheme that maps 8-bit symbols to 10-bit symbols. In some implementations, the cable coupling the hub 114 to the satellites 106 includes multiple transmit and receiving channels such that signal can be transmitted between the hub 114 and satellites 106 using complementary differential signaling.

Using the communication protocol, the satellite 106 transmits recorded data and health status information to the hub 114. The hub 114 can also transmit programming information, power settings, and other configuration information to each of the satellites 106 via the communication protocol. The communication protocol includes a configurable and tiered addressing scheme that enables satellites 106 coupled to a single cable 302 to be addressed. As each of the satellites 106 are coupled to the same cable 302, each satellite 106 receives a signal transmitted by the hub 114 along the cable 302. The hub 114 can encode destination information into a header of signals transmitted along the cable 302. Each satellite 106 receives the signal and reads the header to determine if the signal was intended for the satellite. In some implementations, the communication protocol enables the satellites 106 to be addressed by the hub 114 at a global level, a group level, an individual level, and a component level. At a global level, all the satellites 106 coupled to the cable 302 are addressed. At the group level, a subset of the total satellite population is addressed. For example, the satellites 106 implanted near the patient's right wrist may form a first group and the satellites 106 implanted near the patient's left wrist may form a second group. At the individual level, a single satellite 106 is address. At the component level, components within a specific satellite 106 are addressed. For example, the power settings may be sent to the power system of a specific satellite 106 or configuration setting may be sent to a specific electrode of the satellite 106.

Figure 4:
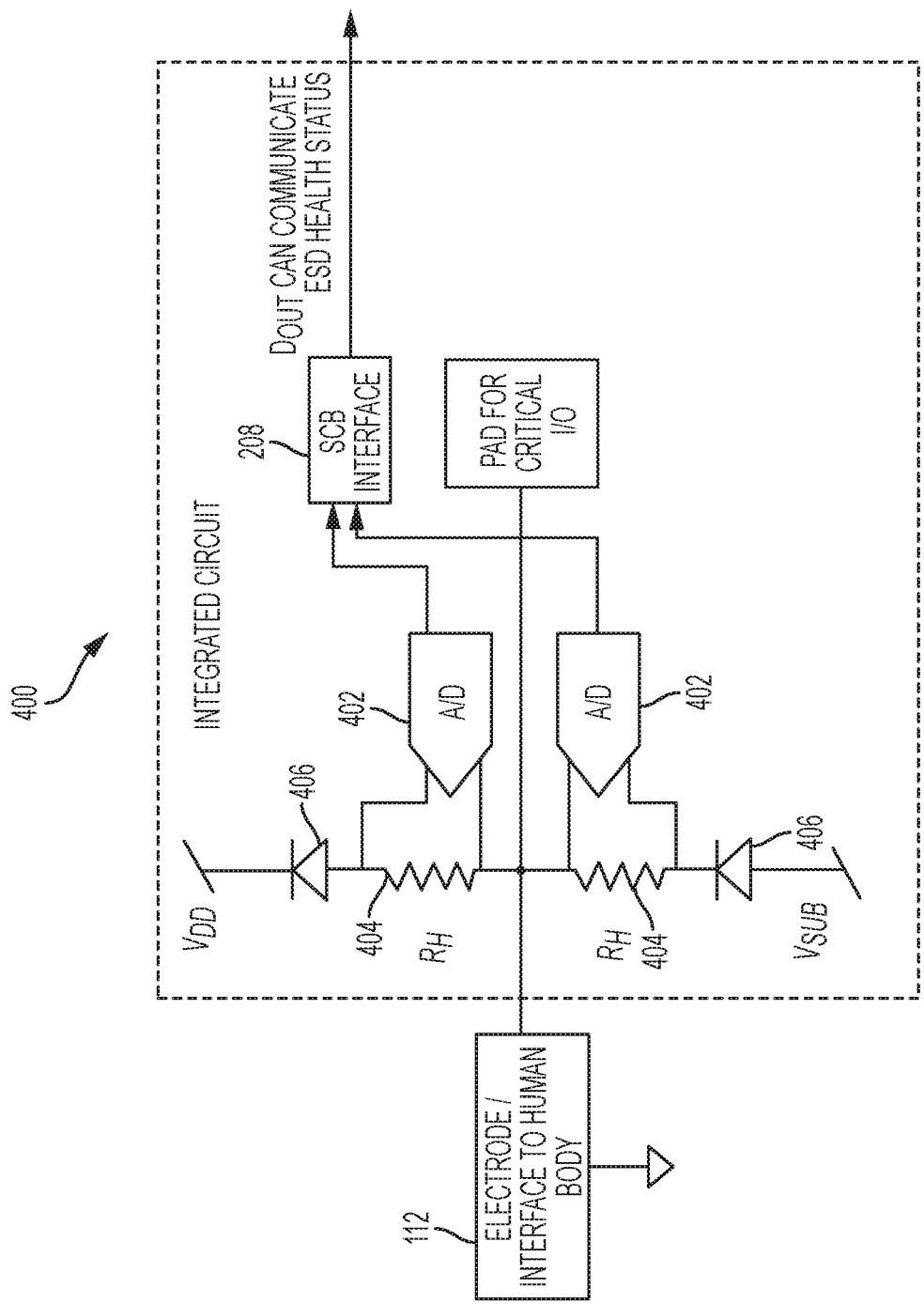
FIG. 4 illustrates an example schematic of a leakage current monitor for use in the system illustrated in FIG. 1.

FIG. 4 illustrates a schematic of an example leakage current monitor 400. The current leakage monitor 400 is implemented as a component of the hub 114 and the satellites 106. The leakage current monitor 400 is configured to monitor input/output (I/O) pathways in the hub 114 and satellites 106 and prevent current from leaking out of the hub 114 and satellites 106 and into the patient's body. For example, a leakage current monitor 400 may be coupled to one or more output pathways of a satellite 106, for example, to output pins of the ICs 202 and 204. The current leakage monitor 400 includes a plurality of analog-to-digital converters (ADCs) 402 and a plurality of current sensing resistors 404. Two electrostatic discharge (ESD) diodes 406 are connected inline with the resistors 404. Each of the ADCs 402 provides a digital signal to the SCB 208. In some implementations, the ESD diodes 406 can be selected to withstand a voltage of 8 kV. In some implementations, the ESD diodes 406 can be selected to withstand a voltage of about 16 kV.

The ADCs 402 are configured to measure a voltage across each of the resistors 404. Under normal operating conditions, when no leak current is present, the voltage across the resistors 404 is substantially zero. When a leak current is present, a voltage is generated across the resistors 404, which the ADCs 402 detect. The ADCs 402 digitize the analog voltage difference across the resistor and transmit the digitized signal to the SCB 208. The SCB 208 can then transmit an indication of a detected leakage current to the hub 114, which can then be transmitted to a medical professional.

In some implementations, when a leak current is detected, the supply of current to the electrode is terminated. In some implementations, the hub terminates the supply to the electrode by terminating the supply of power to an entire satellite with the current leak. In other implementations, the current leakage monitor 400 can include an electrically controllable switch along the I/O pathway to the electrode. When a leak current is detected, the switch can be opened to prevent current from leaking out of the electrode. In these implementations, preventing current flow to a faulty electrode by opening a switch in the satellite can enable the other electrodes to continue to operate. In some implementations, the current leakage monitor 400 has an automatic trip value. In these implementations, when a voltage above the automatic trip value is detected across the resistors 404, the switch to the electrode automatically opens, or power is automatically cut to the electrode to quickly prevent current from leaking into the patient. For example, the I/O pathway of the electrode can include a transistor with an inverter coupled to the transistor's gate. The inverter can be coupled to the ADC 402, such that when the ADC 402 detects a voltage above a predetermined threshold, the transistor prevents current flow to the electrode. In some implementations, the transistor (or switch) is placed along a power trace for the satellite, such that when the predetermined threshold is crossed power to the satellite is suspended. In some implementations, the voltage drop across each resistor 404 is measured by a different ADC 402, and in other implementations, a switching fabric enables a single ADC 402 to monitor the voltage across a plurality of resistors 404. In some implementations, the ADCs 402 continuously monitor the voltage across the resistors 404 and in other implementations, the ADCs monitor the voltage across the resistors 404 intermittently, such during a startup or a system diagnostic phase. In some implementations, the voltage threshold is tied to a threshold current value and the size of the resistor 404 selected for use in the current leakage monitor. For example, the threshold voltage can be set to the voltage that would result from a current of about 100 nA flowing through the resistor 404. In some implementations, the threshold voltage can be set to the voltage that would result from a current of about 25 nA flowing through the resistor 404.

In some implementations, safety regulations require that implanted medical devices not have a single point of failure. Previous medical devices prevent leak current by placing capacitors in series along the electrode I/O paths. This practice can present a number of issues. For example, adding capacitors to each of the channels limits the miniaturization of the implantable devices because the capacitors cannot be miniaturized to the same extent as the other components of the device. This problem can result in a relatively smaller device with few electrode channels or a relatively larger device with a greater number of electrode channels, but prevents the design of relatively small devices with a large number of electrode channels. By actively monitoring the pathways where leak current could occur with the above-described current leakage monitor 400, the systems described herein do not require capacitors along the electrode I/O pathways because the power can be cut to each of the electrodes if a leak current is detected.

Figure 5:
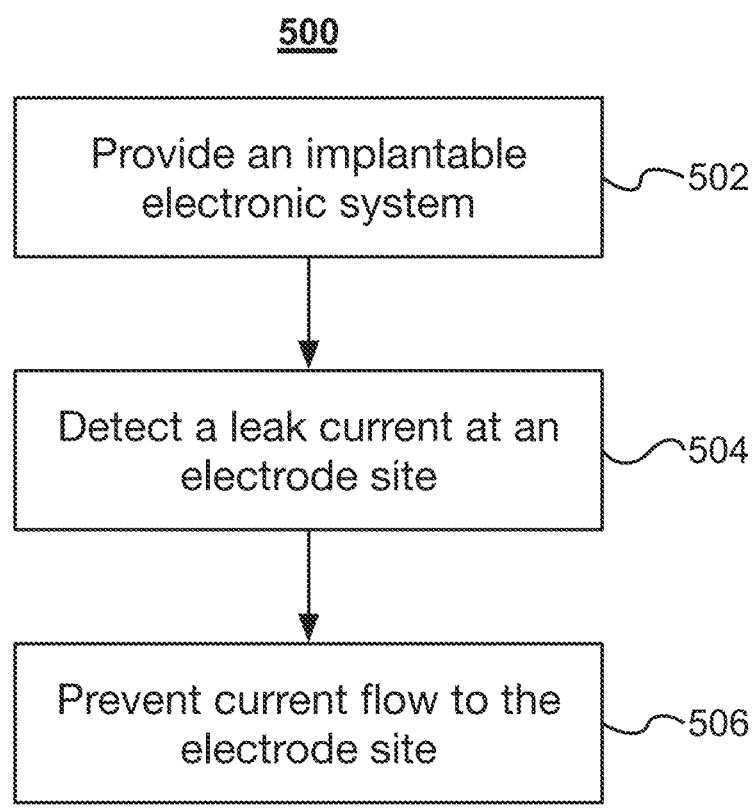
FIG. 5 illustrates a flow chart of an example method for preventing leak current in the system illustrated in FIG. 1.

FIG. 5 illustrates a flow chart of an example method 500 for preventing leak current. The method 500 includes providing an implantable electronic system (step 502). The method also includes detecting a leak current at an electrode site (step 504), and then preventing current flow to the electrode site (step 506).

As set forth above, the method 500 includes providing an implantable electronic system (step 502). In some implementations, the implantable electronic system is the system 100 described above in relation to FIG. 1. For example, the electronic system can include a plurality of satellites that are coupled to a central hub. One or more electrodes can be coupled to each of the satellites. The electrodes are configured to record from and electrically stimulate neural tissue.

The method 500 also includes detecting a leak current at an electrode site (step 504). Also referring to FIG. 4, each of the satellites of the implantable electronic system include a current leakage monitor 400. The current leakage monitor 400 includes two ESD diodes 406 and two resistors 404 coupled in series. When a leak current is present in an I/O pathway of an electrode, a voltage is generated across the resistors 404. The generated voltage is detected by a SCB 208 via ADCs 402.

Next, current flow to the electrode site is prevented (step 506). In some implementations, when the SCB detects a voltage across the resistors, the SCB can locally prevent current flow to the electrode site. For example, the electrode's I/O pathway may include a switch that the SCB electronically throws to prevent current from flowing to the electrode and into the patient. In some implementations, the satellite's SCB can transmit an indication to the central hub that one of its electrode sites is generating a leakage current. The central hub can then report the fault to a medical professional.

The disclosed system and methods may be embodied in other specific forms without departing from the spirit or essential characteristics thereof. The forgoing implementations are therefore to be considered in all respects illustrative, rather than limiting of the invention.

What is claimed:

1. An implantable neural interface system comprising:
   a controller hub comprising a first communication chip;
   a plurality of electrodes, each configured to be secured directly to neural tissue; and
   a plurality of satellite devices, each coupled to the controller hub via a respective connector, and each comprising:
      an output pathway coupled to a respective one of the plurality of electrodes;
      a leakage current monitor coupled to the output pathway and configured to:
         detect a leakage current along the output pathway and measure a value of the leakage current, and
         generate a digital signal based on the measured value of the leakage current; and
      a second communication chip communicatively coupled to the first communication chip, wherein the second communication chip is configured to receive the digital signal from the leakage current monitor.

2. The system of claim 1, wherein the leakage current monitor of each satellite device is configured to divert power away from the output pathway of that satellite device responsive to detecting the leakage current.

3. The system of claim 1, wherein the leakage current monitor is configured to cause the second communication chip to transmit, to the first communication chip of the controller hub, an indication of the detected leakage current.

4. The system of claim 3, wherein the first communication chip of the controller hub is configured to, responsive to receiving the indication of the detected leakage current, transmit a warning message to an external receiver.

5. The system of claim 1, wherein the leakage current monitor of each satellite device comprises two electrostatic discharge (ESD) diodes coupled to the output pathway.

6. The system of claim 5, wherein the leakage current monitor of each satellite device comprises an analog-to-digital converter coupled across a resistor coupled to one of the ESD diodes.

7. The system of claim 1, wherein only a single cable forms the respective connector coupling each of the plurality of satellite devices to the controller hub.

8. The system of claim 1, wherein the first and second communication chips are configured to communicate using a 3-wire protocol.

9. The system of claim 1, wherein the first and second communication chips are configured to encode and decode communication signals using a DC-balanced encoding scheme.

10. The system of claim 9, wherein the DC-balanced encoding scheme is a 4b6b encoding scheme.

11. The system of claim 3, wherein the controller hub is configured to receive the indication from one of the satellites about the measured value of the leakage current at the satellite via the first communication chip of the controller hub and to terminate supplying power to the satellite responsive to the received indication indicating the measured leakage current exceeds a threshold value.

12. The system of claim 1, wherein each of the satellite devices further comprises:
    an additional output pathway coupled to the respective connector between that satellite device and the controller hub; and
    an additional leakage current monitor configured to detect an additional leakage current along the additional output pathway.

13. The system of claim 1, wherein the controller hub further comprises:
- an additional output pathway, coupled to a corresponding one of the connectors coupled between the controller hub and the plurality of satellite devices; and
- an additional leakage current monitor configured to detect an additional leakage current along the additional output pathway.

14. The system of claim 13, wherein the first communication chip of the controller hub is further configured to, responsive to the detection of the additional leakage current by the additional leakage current monitor, transmit a warning message to an external receiver.

15. The system of claim 13, wherein the additional leakage current monitor is configured to divert power away from the additional output pathway of the controller hub, responsive to detecting the additional leakage current.

* * * * *